United States Patent
Priestman

(10) Patent No.: US 9,376,654 B2
(45) Date of Patent: Jun. 28, 2016

(54) BIOCONTAINER

(75) Inventor: Michael Priestman, Santa Maria, CA (US)

(73) Assignee: Meissner Filtration Products, Inc., Camarillo, CA (US)

( * ) Notice: Subject to any disclaimer, the term of this patent is extended or adjusted under 35 U.S.C. 154(b) by 23 days.

(21) Appl. No.: 13/406,311

(22) Filed: Feb. 27, 2012

(65) Prior Publication Data

US 2012/0224450 A1    Sep. 6, 2012

Related U.S. Application Data

(60) Provisional application No. 61/449,027, filed on Mar. 3, 2011.

(51) Int. Cl.

| | | |
|---|---|---|
| B29D 22/00 | (2006.01) |
| C12M 1/00 | (2006.01) |
| A61J 1/10 | (2006.01) |
| B01F 11/00 | (2006.01) |
| B01F 15/00 | (2006.01) |
| B65D 30/24 | (2006.01) |
| B65D 33/02 | (2006.01) |
| C12M 3/06 | (2006.01) |

(52) U.S. Cl.
CPC . *C12M 23/14* (2013.01); *A61J 1/10* (2013.01); *B01F 11/0017* (2013.01); *B01F 15/0085* (2013.01); *B01F 15/00896* (2013.01); *B65D 31/147* (2013.01); *B65D 33/02* (2013.01); *C12M 27/16* (2013.01)

(58) Field of Classification Search
CPC ...... B65D 77/065; B65D 77/06; B65D 33/02; A61J 1/10
USPC ........... 366/219, 237, 239; 428/35.2; 383/903
See application file for complete search history.

(56) References Cited

U.S. PATENT DOCUMENTS

| | | | |
|---|---|---|---|
| 3,297,152 A * | 1/1967 | Corella et al. | 206/221 |
| 4,140,162 A * | 2/1979 | Gajewski | 524/291 |
| 4,557,377 A * | 12/1985 | Maloney | 206/219 |
| 4,909,478 A * | 3/1990 | Steer | 251/352 |
| 6,071,005 A * | 6/2000 | Ekambaram et al. | 366/173.2 |
| 6,544,788 B2 * | 4/2003 | Singh | 435/383 |
| 2003/0059128 A1 * | 3/2003 | Vangedal-Nielsen | 383/4 |

FOREIGN PATENT DOCUMENTS

| | | |
|---|---|---|
| EP | 0 578 086 A1 | 1/1994 |
| EP | 1 512 458 A1 | 3/2005 |
| WO | WO 2007/142887 A1 | 12/2007 |
| WO | WO 2009/042428 A1 | 4/2009 |
| WO | WO 2011/005773 A2 | 1/2011 |

OTHER PUBLICATIONS

European Patent Office; European Search Report for Application No. 12158072.4-1521; dated May 29, 2012; 5 Pages.

* cited by examiner

*Primary Examiner* — Tony G Soohoo
*Assistant Examiner* — Anshu Bhatia
(74) *Attorney, Agent, or Firm* — Lewis Roca Rothgerber Christie LLP

(57) ABSTRACT

A biocontainer. The biocontainer includes a first flexible wall, a second flexible wall opposite the first flexible wall, a first end, a second end opposite the first end, a third end extending between the first and second ends, a fourth end extending between the first and second ends and opposite the third end, and a first relief section extending from the first end.

23 Claims, 13 Drawing Sheets

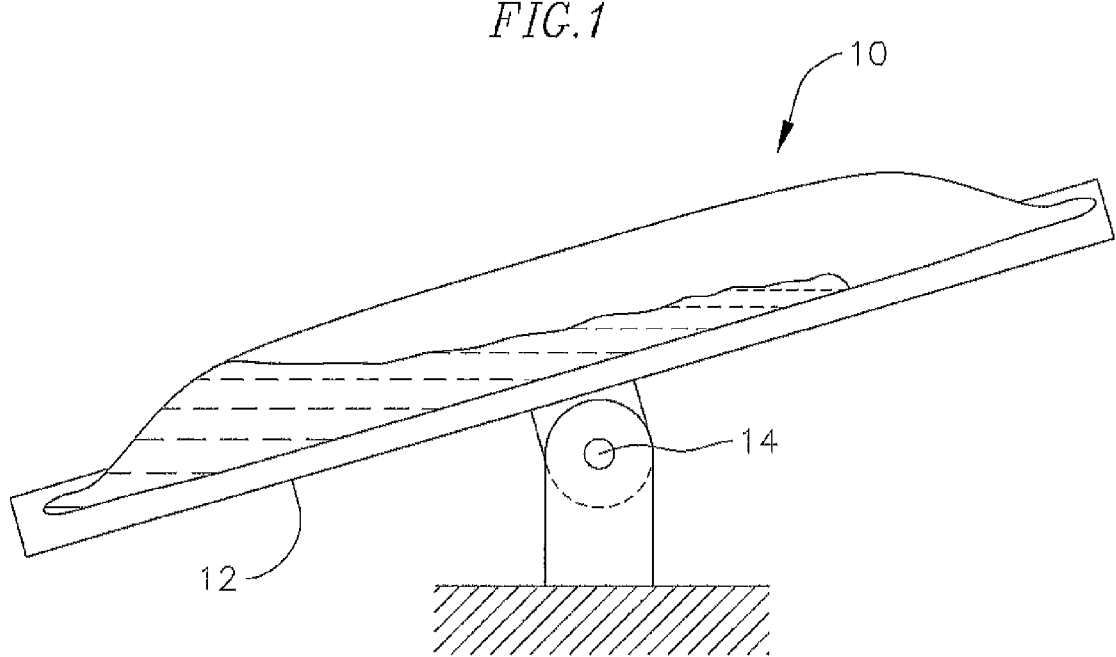

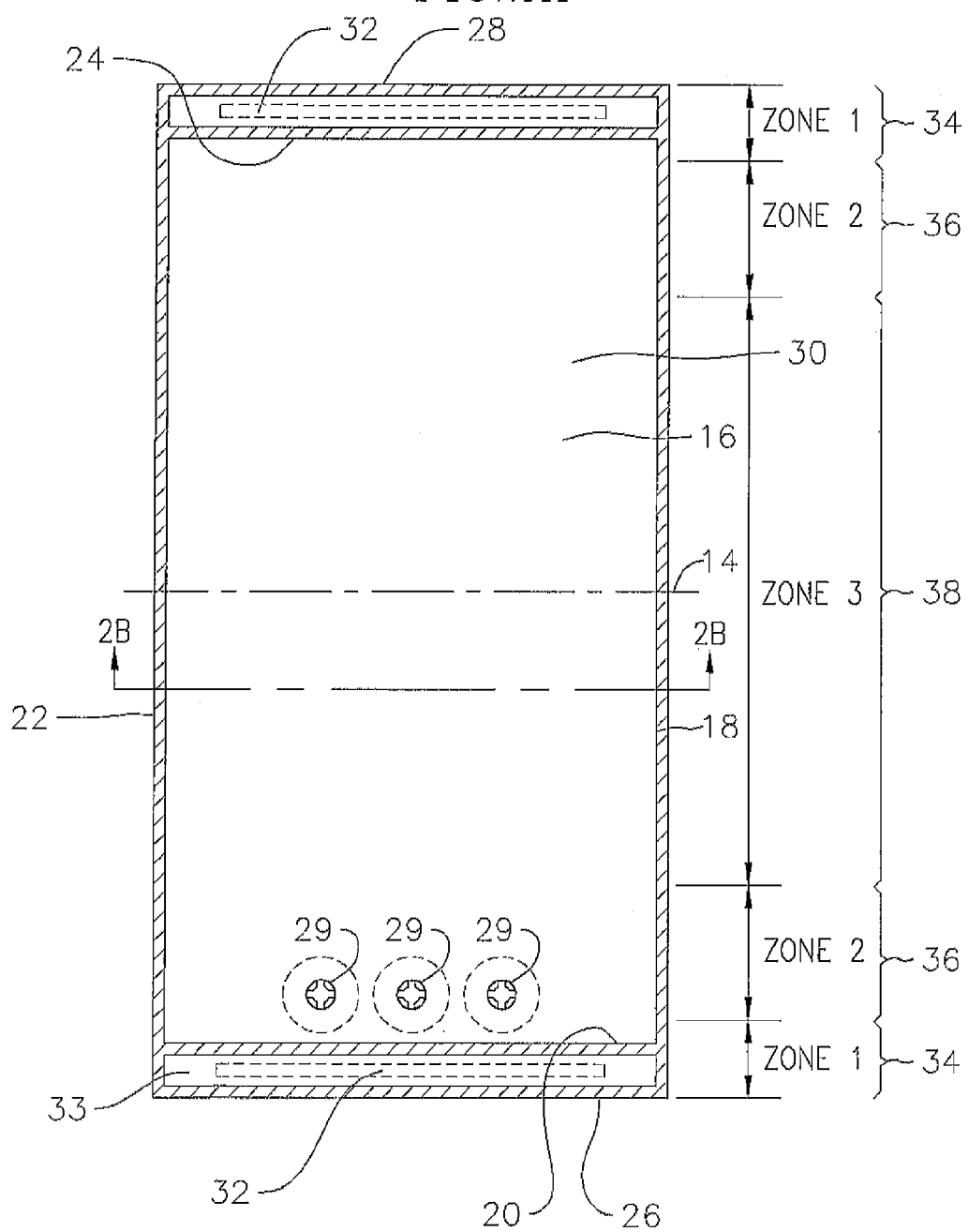
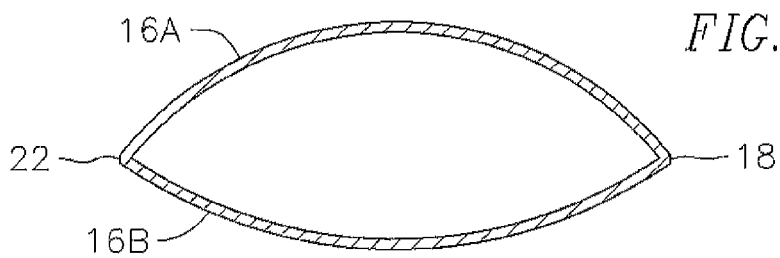

BIOCONTAINER

CROSS-REFERENCE TO RELATED APPLICATION

This application is based upon and claims priority on U.S. Provisional Application No. 61/449,027, filed on Mar. 3, 2011, the contents of which are fully incorporated herein by reference.

BACKGROUND OF INVENTION

Single-use biocontainers 10 as shown in FIG. 1 are manufactured for use in conjunction with hardware designed around a platform 12 that oscillates in a rocking or seesaw motion, as for example described in U.S. Pat. Nos. 6,190,913, 6,544,788 and 7,195,394, the contents of which are fully incorporated herein by reference. This rocking motion, typically on the order of 12 to 20 degrees total sweep at a rate of 4-25 cycles per minute, is transferred to the biocontainer about an axis 14 which in turn imparts motion to a fluid and/or gas contained therein. For convenience the term "fluid" as used hereafter after refers to a fluid, or a gas, or to the combination of a fluid and, a gas. The imparted fluid motion is often used to accomplish unit processing steps within the biopharmaceutical industry, e.g. mixing or cell culture operations. The latter of these examples can require extended processing times on the order of one week to three months plus during which the oscillatory rocking motion is repeated constantly. These extended operating periods subject the biocontainer to high cyclical stress loads which can lead to breaches in the fluid containment area.

The biocontainers manufactured for use in conjunction with the aforementioned rocking platforms are typically single-use bags of construction such as shown in FIG. 2A. It should be noted that "bag(s)," "biocontainer(s)" and "biocontainer bag(s)" are used interchangeably herein. Representative biocontainers are two-dimensional in nature and are manufactured from two sheets (films) 16A, 16B of polymeric film 16 having dimensions (H1×W1) that are welded together along weld lines 18, 20, 22, 24, 26 and 28 to create a contained seal geometry. The welds along the weld lines form seams. Thus, the terms "weld lines" and "seams" are used interchangeably herein to refer to the area of bonding between the two sheets of polymeric film. These biocontainers contain porting 29, for fluid ingress and egress as well as gas exchange, which are welded within a fluid containment area 16 (H2×W2) defined between weld lines 18, 20, 22 and 24. The weld lines form seams. Additionally, the biocontainers include rigid support rods 32 at each end which are sealed into segregated areas 33 of the biocontainer (H3×W3) defined between weld lines 20, 26, 18 and 22, and 24, 26, 18 and 22, respectively. The support rods are used to help secure the biocontainer to the rocking platform. The rocking platform includes at least two clamps, such that each clamp clamps on the segregated areas and specifically the rod in such areas for securing each end of the biocontainer in place.

When the biocontainers are deployed, i.e. secured to the rocking platform and filled to capacity with a fluid, three distinct zones 34, 36 and 38 form. A first zone 34 also referred to herein as "Zone 1" is a two-dimensional zone in that it remains relatively flat. This area of the flexible single-use biocontainer is constrained by the rocking platform clamp and thus retains it two-dimensional "flat" shape. A second zone 36 referred to herein as "Zone 2" is a transitional zone. In this area, the biocontainer shape transitions between a generally two-dimensional shape at one end and the fully developed three-dimensional shape at its other end. A third zone 38 also referred to herein as "Zone 3" is a three-dimensional zone. In this zone, the biocontainer has developed its three-dimensional shape and has a cross-sectional shape along its length which is oval as a result of the fluid fill volume.

With the current biocontainers depicted in FIG. 2A, folding, crumpling and/or other undesirable film shapes can occur in Zone 2, i.e., in the transitional zone, due to geometry constraints associated with the transition between the two-dimensional end portion and the three-dimensional center portion. These undesirable film shapes create stress concentrations which when combined with the cyclical stress associated with the oscillatory motion of the fluid within the biocontainer, serve to decrease the service life of the biocontainer. Premature failures are believed to be due to either, a stress crack in the polymeric film material at a stress concentration point, or abrasion between the two films at a contact point. Both of these failure mechanisms manifest themselves in a repeatable nature in the four identified areas D in the transitional zones 36 of the current biocontainers and are directly attributable to the aforementioned undesirable film shapes in the transitional zones (Zones 2).

SUMMARY OF THE INVENTION

In an exemplary embodiment a biocontainer is provided including a first flexible wall, a second flexible wall opposite the first flexible wall, a first end, a second end opposite the first end, a third end extending between the first and second ends, a fourth end extending between the first and second ends and opposite the third end, and a first relief section extending from the first end, wherein the first relief section is connects the first flexible wall to the second wall. In another exemplary embodiment, the first flexible wall is separate from the second flexible wall and is connected to the second flexible wall. In yet another exemplary embodiment, the first flexible wall is connected to the second flexible wall along at least one of the ends. In a further exemplary embodiment, the first relief section includes a separate member connected to the first flexible wall and to the second flexible wall. In yet a further exemplary embodiment, the first relief section is formed by connecting the first flexible wall directly to the second flexible wall. In one exemplary embodiment, the first relief section begins and ends at the first end. In another exemplary embodiment, the biocontainer also includes a second relief section, along which the first wall is connected to the second wall, proximate the fourth end beginning from and ending at the first end, a third relief section, along which the first wall is connected to the second wall, proximate the third end beginning from and ending at the second end, and a fourth relief section, along which the first wall is connected to the second wall, proximate the fourth end beginning from and ending at the second end. In yet another exemplary embodiment, each of the relief sections is semi-circular in plan view. In a further exemplary embodiment, when the bag is filled with a fluid, the biocontainer has a depth as measured between the first and second walls, wherein the depth increases from each of the third and fourth ends in a direction along each of the first and second ends transitioning between minimum or no depth at each of the third and fourth ends to an expanded depth at a distance from each of the third and fourth ends, wherein each of the first, second, third and fourth seams are located along a length within the distance. In one exemplary embodiment, the expanded depth is a maximum depth. In a further exemplary embodiment, each of the first, second, third and fourth relief sections are curved or define a geometric shape in plan view. In yet a further exemplary embodiment, each of the first, second, third and fourth relief sections intersects its corresponding first or second end at an external angle greater than 90°. In another exemplary embodiment, the biocontainer also includes a seam extending from the third to the fourth ends and being spaced apart from the first and second ends. In yet a further exemplary embodiment, the first relief section aids in the mixing of a fluid within the biocontainer. In one exemplary embodiment, a seam is defined along each of the ends connecting the first flexible wall to the second flexible wall. In another exemplary embodiment, a single piece of flexible material is bent over itself and connected along a seam to form the first flexible wall and the second flexible wall.

In yet another exemplary embodiment, the first flexible wall is separate from the second flexible wall and the biocontainer further includes a first seam along the first end along which the first wall is connected to the second wall, a second seam along the second end along which the first wall is connected to the second wall opposite the first seam, a third seam along the third end along which the first wall is connected to the second wall and extending between the first and second seams, a fourth seam along the fourth end along which the first wall is connected to the second wall and extending between the first and second seams and being opposite the third seam, and a fifth seam defining the first relief section, along which the first wall is connected to the second wall, proximate the third seam beginning from and ending at the first seam, wherein the biocontainer has a length along the first seam and a width along the third seam as measured between the third and fourth seams, wherein each seam connects the first flexible wall to the second flexible wall. In a further exemplary embodiment, the biocontainer also includes a sixth seam, along which the first wall is connected to the second wall, proximate the fourth seam beginning from and ending at the first seam, a seventh seam, along which the first wall is connected to the second wall, proximate the third seam beginning from and ending at the second seam, and an eight seam, along which the first wall is connected to the second wall, proximate the fourth seam beginning from and ending at the second seam. In one exemplary embodiment, each of the seams is semi-circular in plan view. In another exemplary embodiment when the biocontainer is filled with a fluid, the biocontainer has a depth as measured between the first and second walls, wherein the depth increases from each of the third and fourth seams in a direction along each of the first and second seams transitioning between minimum or no depth at each of the third and fourth seams to an expanded depth at a distance from each of the third and fourth seams, wherein each of the fifth, sixth, seventh and eight seams are located along a length within the distance. In yet another exemplary embodiment, each of the fifth, sixth, seventh and eighth seams are curved or define a geometric shape in plan view. In one exemplary embodiment, each of the fifth, sixth, seventh and eighth seams intersects its corresponding first or second seam at an external angle greater than 90°.

In any of the aforementioned exemplary embodiments, the biocontainer may include a rod proximate at least one of said third and fourth ends or seams. Furthermore any of the aforementioned exemplary embodiment biocontainers may be clamped proximate its third and fourth sides or seams to an oscillating platform.

BRIEF DESCRIPTION OF THE DRAWINGS

FIG. 1 is a schematically depicted end view of a biocontainer mounted on a rocking platform.

FIG. 2A is a top view of a biocontainer of the present invention.

FIG. 2B is a cross-sectional view taken along arrow 2B-2B in FIG. 2A of the biocontainer shown in FIG. 2A in an inflated state.

DETAILED DESCRIPTION

Figure 4:
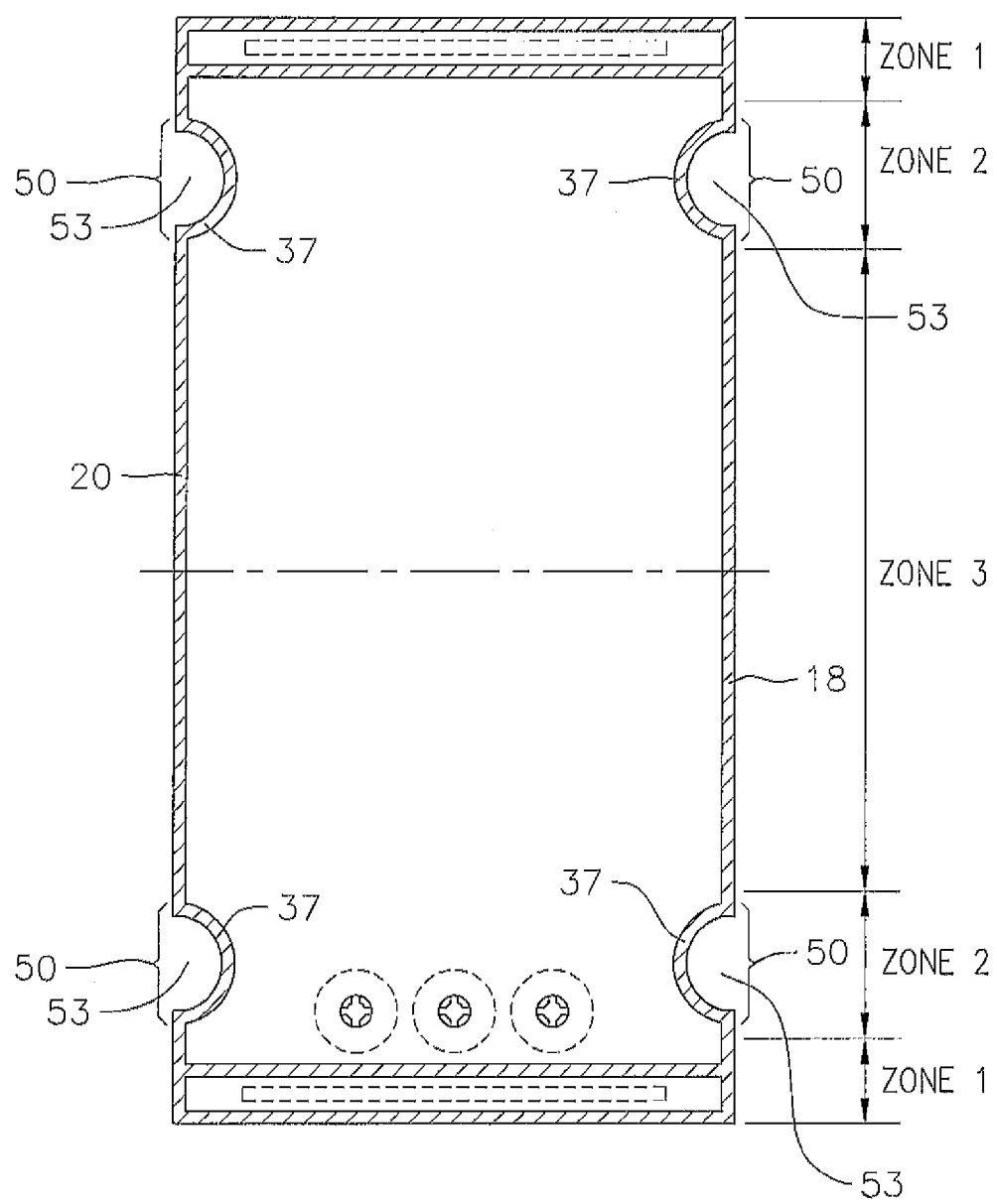
Figure 5:
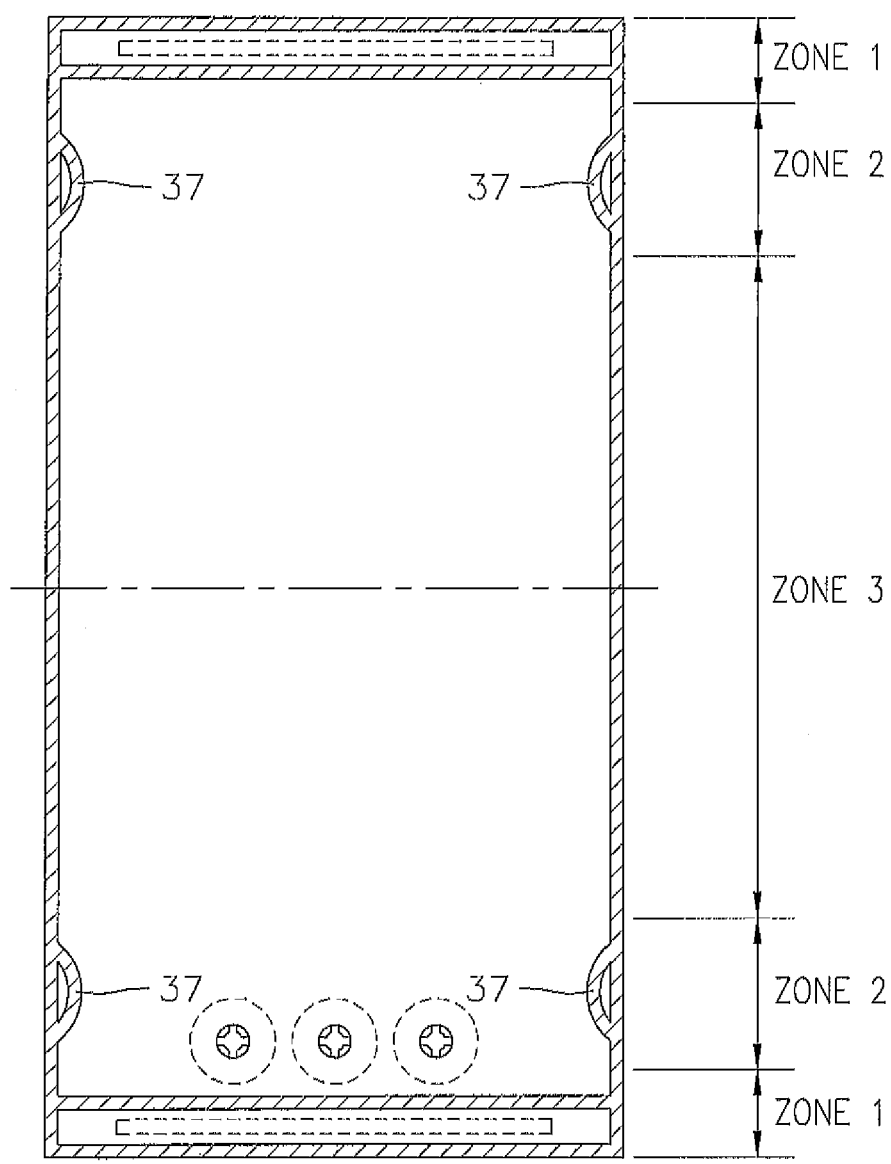
Figure 6:
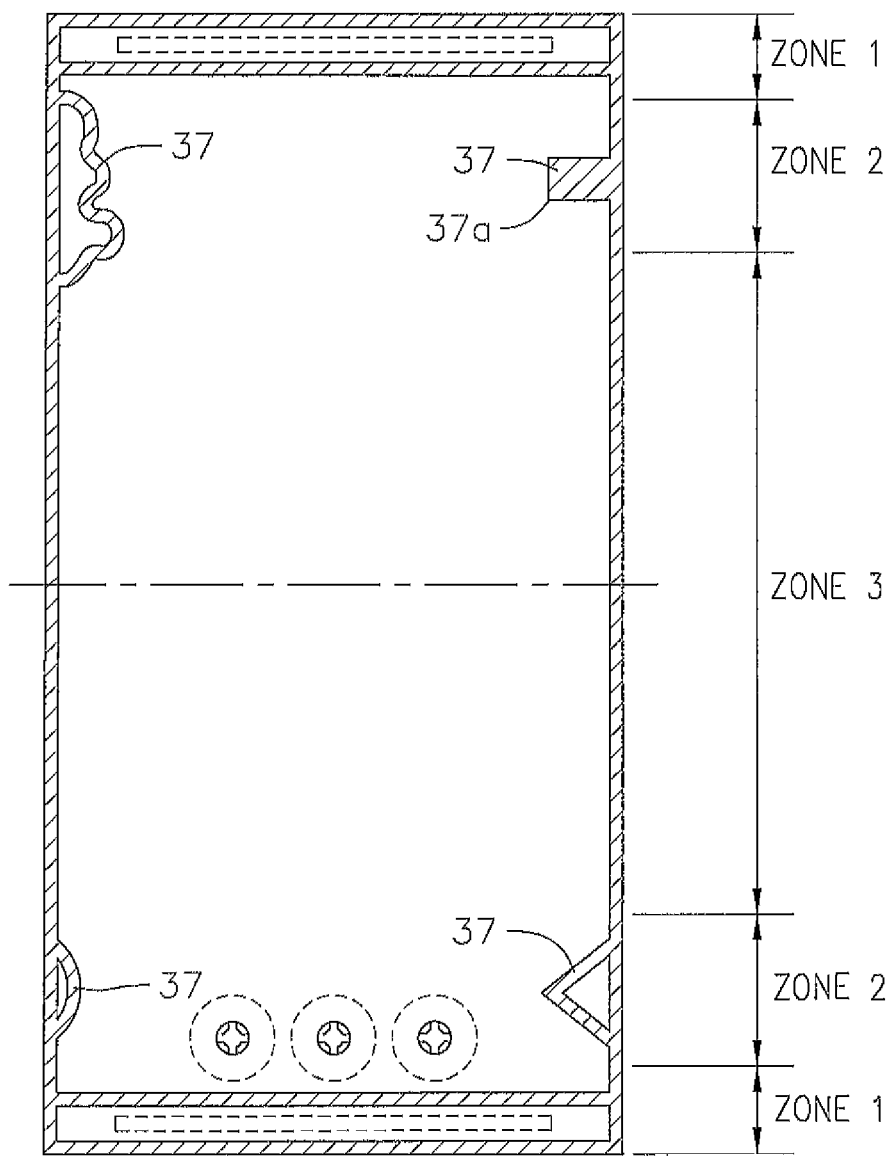

Applicants have invented a biocontainer bag that overcomes the deficiencies of the current biocontainer bags. Applicants have been able to achieve this by including relief sections in the transitional zones (Zones 2) 36, as for example shown in FIG. 3. The locations of the transitional zones for a given bio container dimensions may be easily determined by filling the bag with a fluid. As discussed when the biocontainer bag 10 is filled, the transitional zones 36 is the zone between the generally two-dimensional flat end portions (Zone 1) 34 of the bag to the full three-dimensional center portion (Zone 3) 38 of the bag. In an exemplary embodiment, four relief sections 37 are provided, two extending from each of the weld lines 18 and 22, respectively. First relief sections 42, 46 are formed at the transitional zone proximate one end of the biocontainer and second relief sections 44, 48 are formed at the transitional zone proximate the opposite end of the biocontainer. Each relief section is formed by welding the two film sheets together along the curve extending from its corresponding weld line 18, 22 (i.e., beginning from and ending at its corresponding weld line). Welding of such film sheets is accomplished by using welding methods known in the art. In an exemplary embodiment, each relief section has a semi-circular shape. In an exemplary embodiment, a semi-circular shape has a radius not greater than one half of the length 51 of the transitional zone 36 as measured along the weld lines 18 and 22. In another exemplary embodiment, the bag may not be welded along any portion 53 of a section 50 between the beginning and end of each relief section along each of the weld lines 18 and 20, as for example shown in FIG. 4. In other exemplary embodiments as for example shown in FIG. 5, the relief sections 37 may be formed by welding along a circular arc that is less than a semi-circle. In another exemplary embodiment, the relief sections 36 may be formed by welding along other geometric shapes, as for example an elliptical shape, or an angular shape so as to form a triangle, or a free-flowing shape, or a rectangular or square shape. In other exemplary embodiments as shown in FIG. 6, the interior of the defined shape of the relief section may also be welded to define a solid shape, as for example shape 37a. It is also desirable that an external angle 41 between the weld lines 18 and 22, and the relief section is 90 degrees or greater. It is believed that if the external angle is smaller than 90 degrees, as for example by forming a relief section by welding along a circular arc which is greater than a semi-circle, an area of intersection between the weld lines 18 and 22 and the relief section would create an area where fluid stagnation can occur. Such stagnation can be detrimental to the actual processing that the biocontainer needs to accomplish, such as mixing or cell culture operations.

These relief sections in an exemplary embodiment provide for a biocontainer which does not form any, or which has a reduced number of folds or crumples or other undesirable film shapes when filled with a fluid. Applicants have discovered by eliminating or reducing these folds, crumples or undesirable film shapes, the life span of the biocontainer is increased. In addition, applicants believe that these relief sections cause a change of direction in the fluid during the rocking motion. In other words, as the fluid contacts these relief sections during the rocking motion, the fluid is caused to change its direction and thus, better mix. As such, use of the inventive biocontainers result in better processing of the fluid which is being processed within the biocontainer during mixing or cell culture operations. Thus, another advantage of the present invention is that the relief sections improve the mixing and processing accomplished by the biocontainers. In this regard, the processing time required for processing such fluid using the inventive biocontainers may be reduced.

In the exemplary embodiments where the relief sections are semi-circular, such sections have a radius 56 that is proportional to the length (H2) 54 and the length 51 of the transitional zone 36. However, applicants also believe that optimum length of the radius 56 may also be affected by the ratio of the width 52 to the length 54. In an exemplary embodiment, the location of a center 58 of each semi-circular relief section is located at a distance 60 from an end 62 of the biocontainer bag from which end the length 54 is measured. This distance 60 is also proportional to the length 54 but it is believed that it is also affected by the ratio of the width 52 to the length 54. In an exemplary embodiment, each relief section occupies at least a portion of the length of the transitional zone. In another exemplary embodiment, each relief section is confined within a transitional zone. Applicants believe that the distance 60 is at a maximum for square biocontainers, i.e., when biocontainers having a width 52 equal to the length 54.

Figure 7:
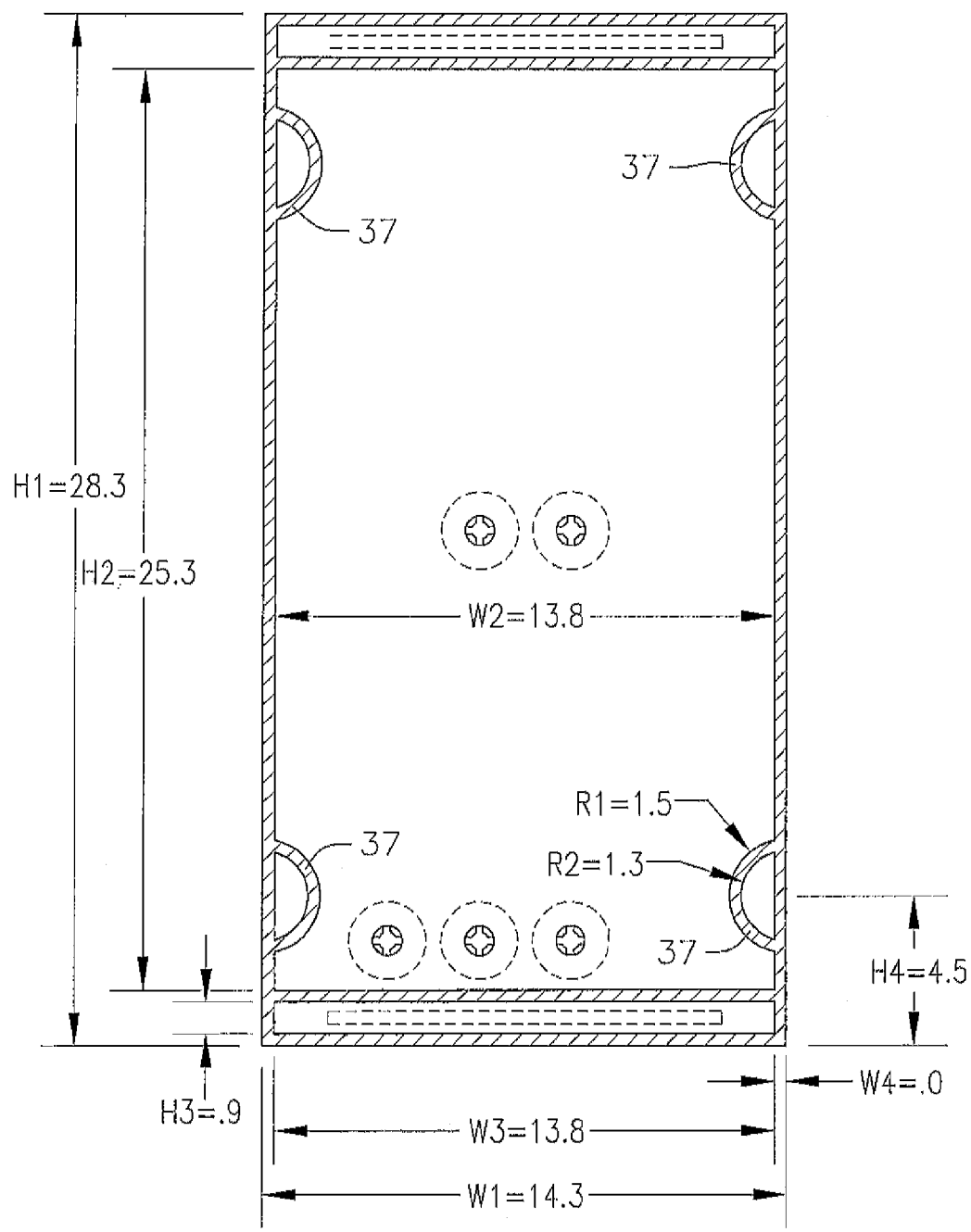
Figure 8:
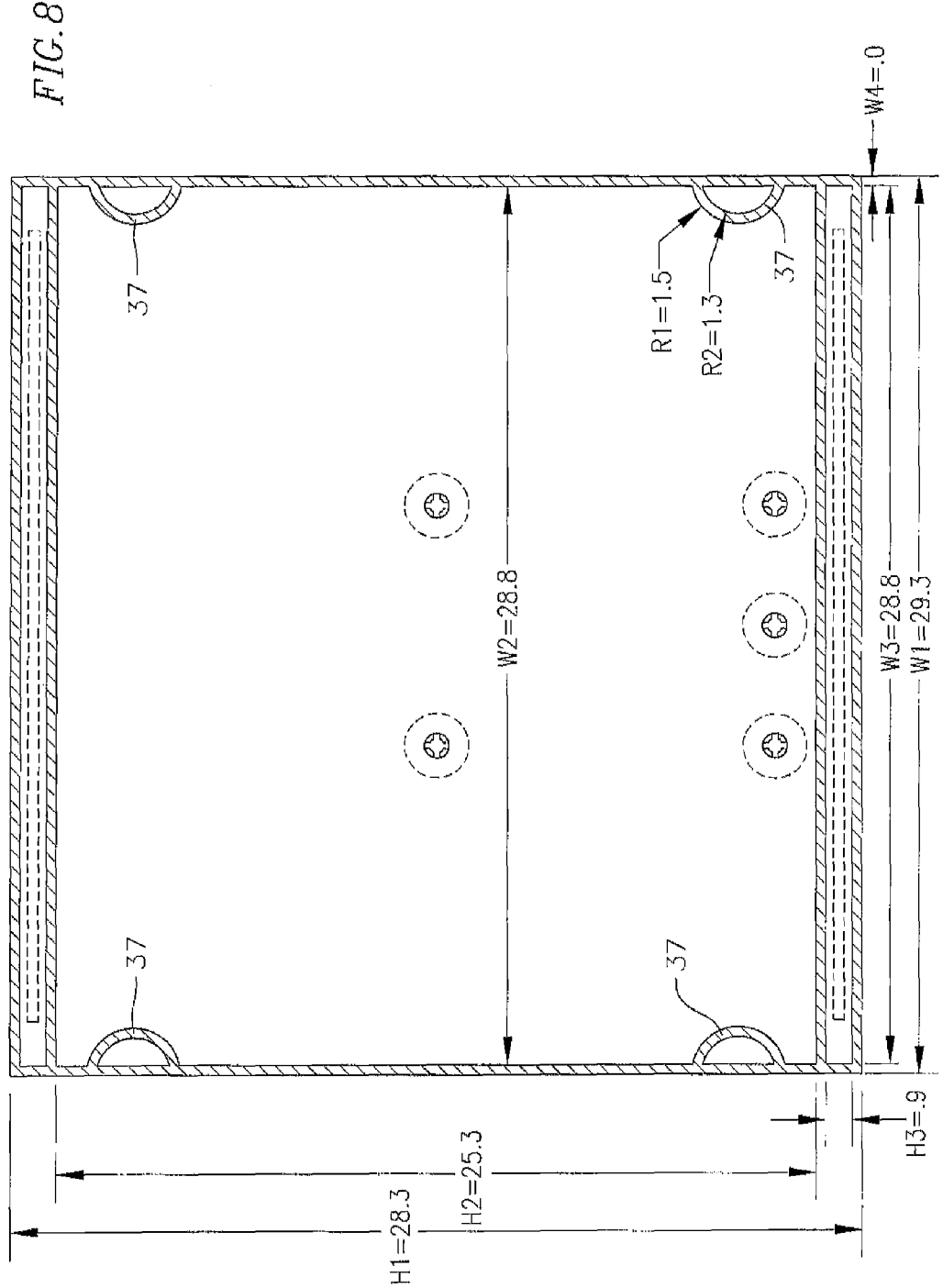
Figure 9:
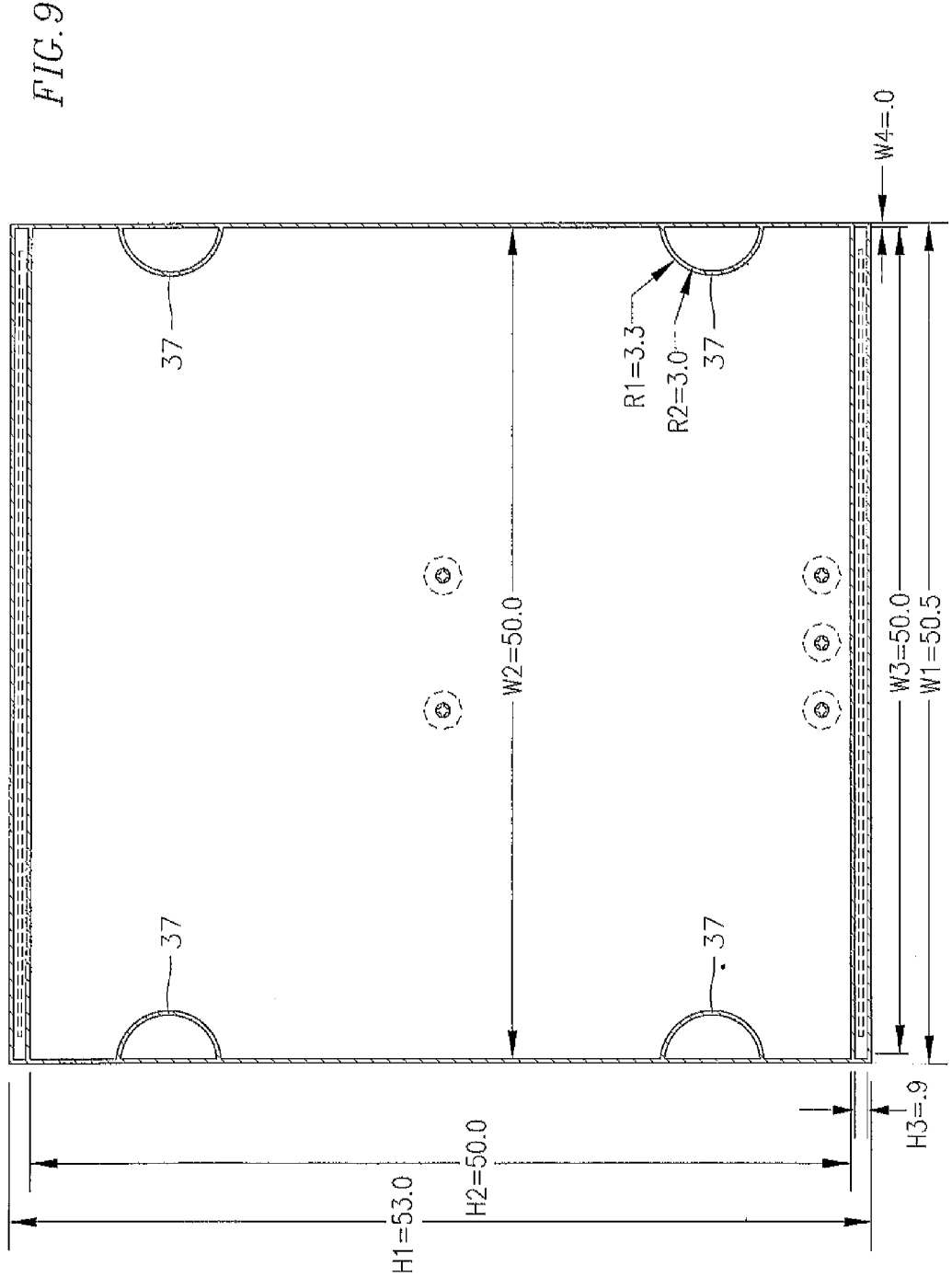

In an exemplary embodiment relief sections, their dimensions and locations for a 22 L biocontainer, a 50 L biocontainer, and a 300 L biocontainer, are shown in FIGS. 7, 8 and 9, respectively. The dimensions of the biocontainer and relief sections are provided in inches, unless otherwise specified.

Figure 12:
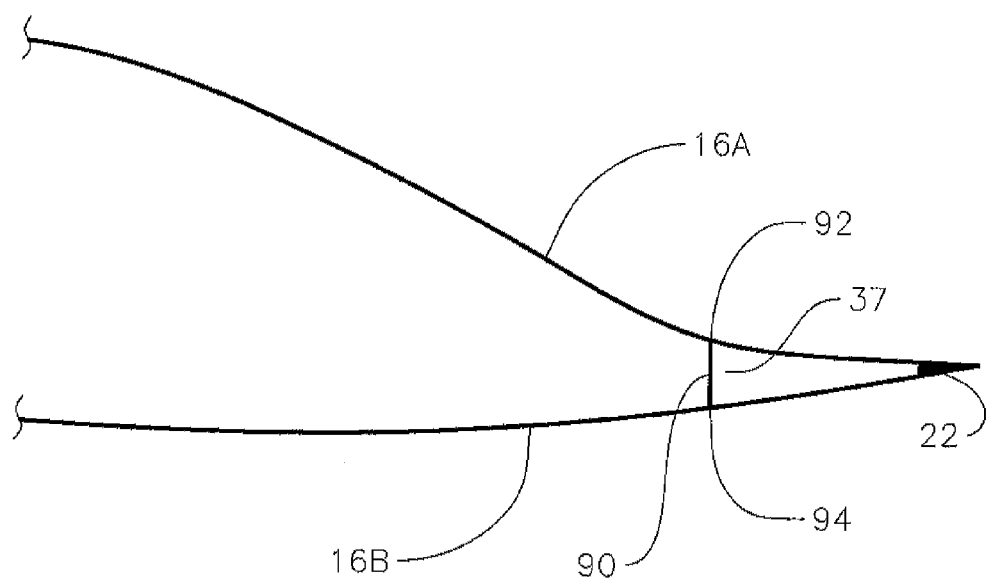
FIG. 12 is a partial cross-sectional view of another exemplary embodiment biocontainer of the present invention.

In another exemplary embodiment, either of the aforementioned relief zones 37 is formed by welding or otherwise connecting the film sheets 16A, 16B together via another member 90 such as a gusset or other piece of plastic as shown in FIG. 12. The gusset or plastic may itself be a piece of film. This member is attached or welded to film sheets 16A and 16B forming seams 92 and 94, respectively and limits the separation of the upper wall and lower walls when the bag is filled with a fluid.

Figure 3:
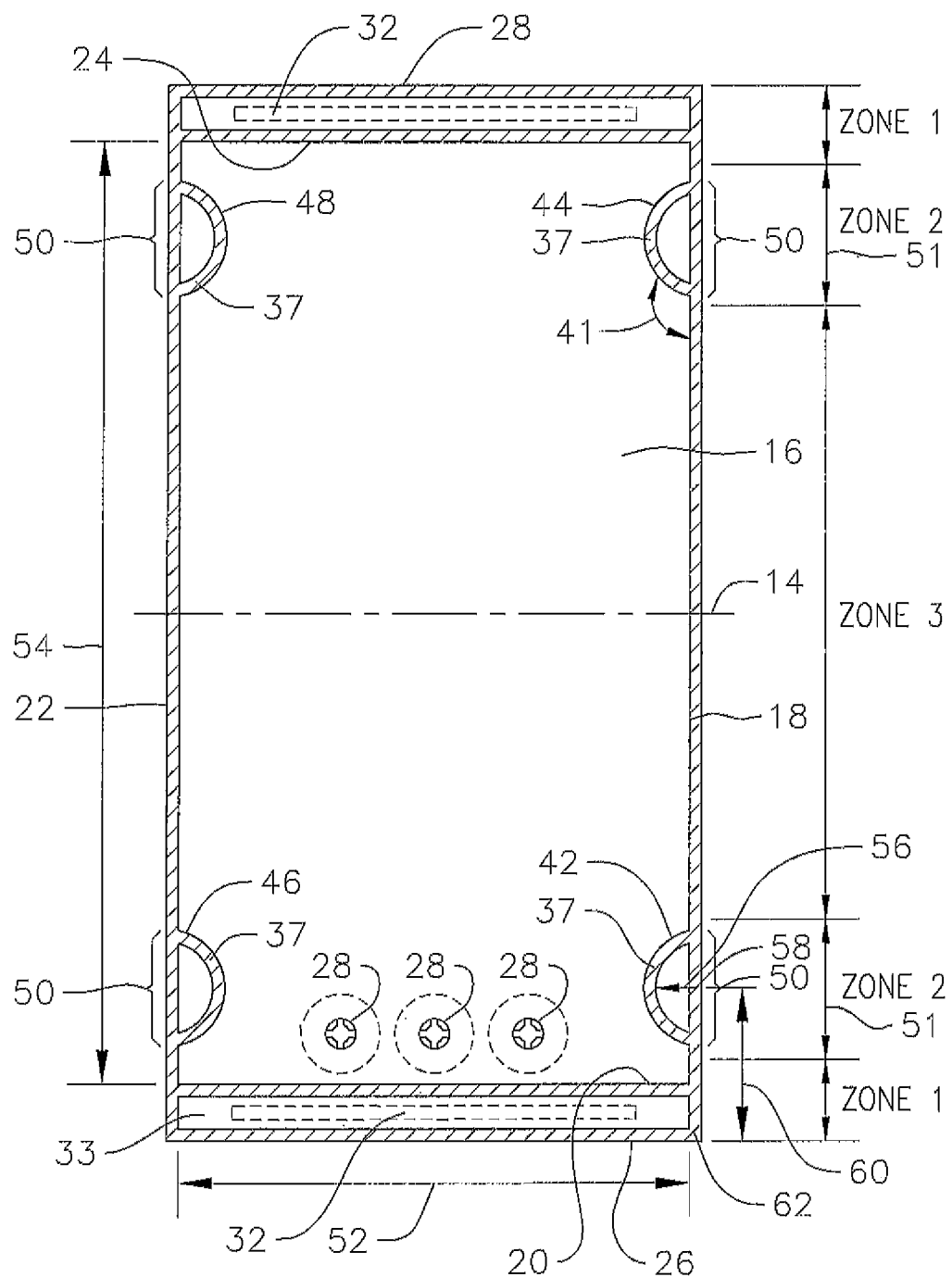
FIGS. 3-11 are top views of an exemplary embodiment biocontainers of the present invention.
Figure 10:
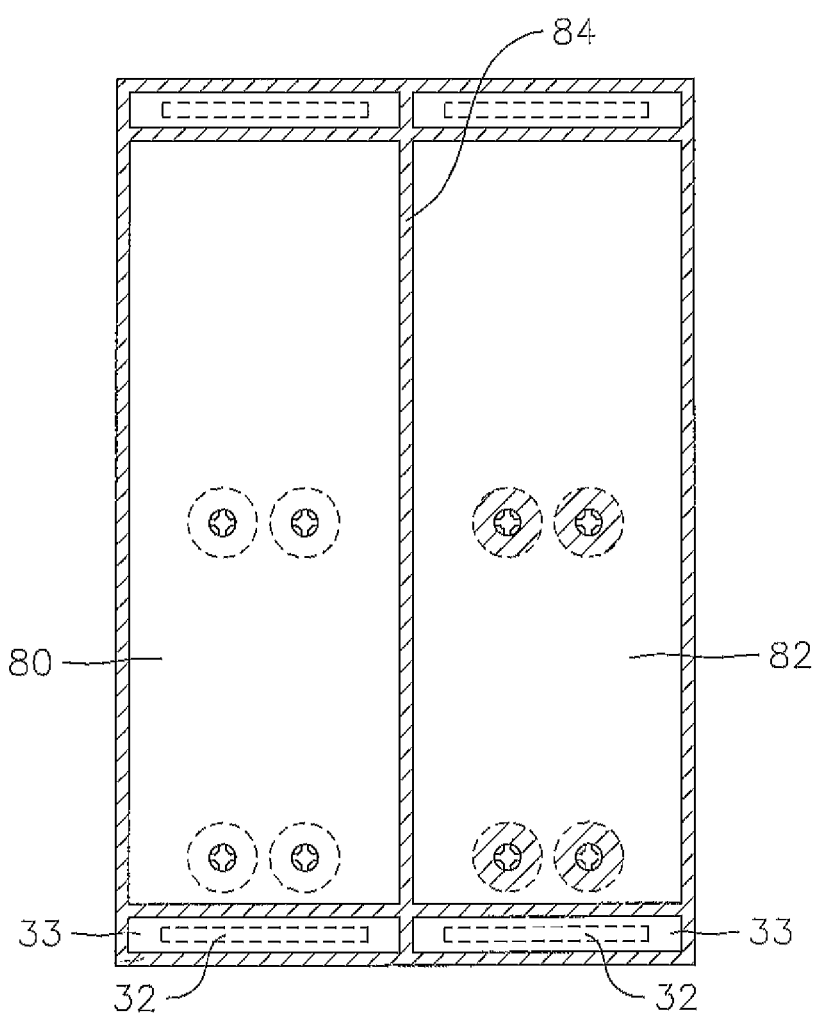
Figure 11:
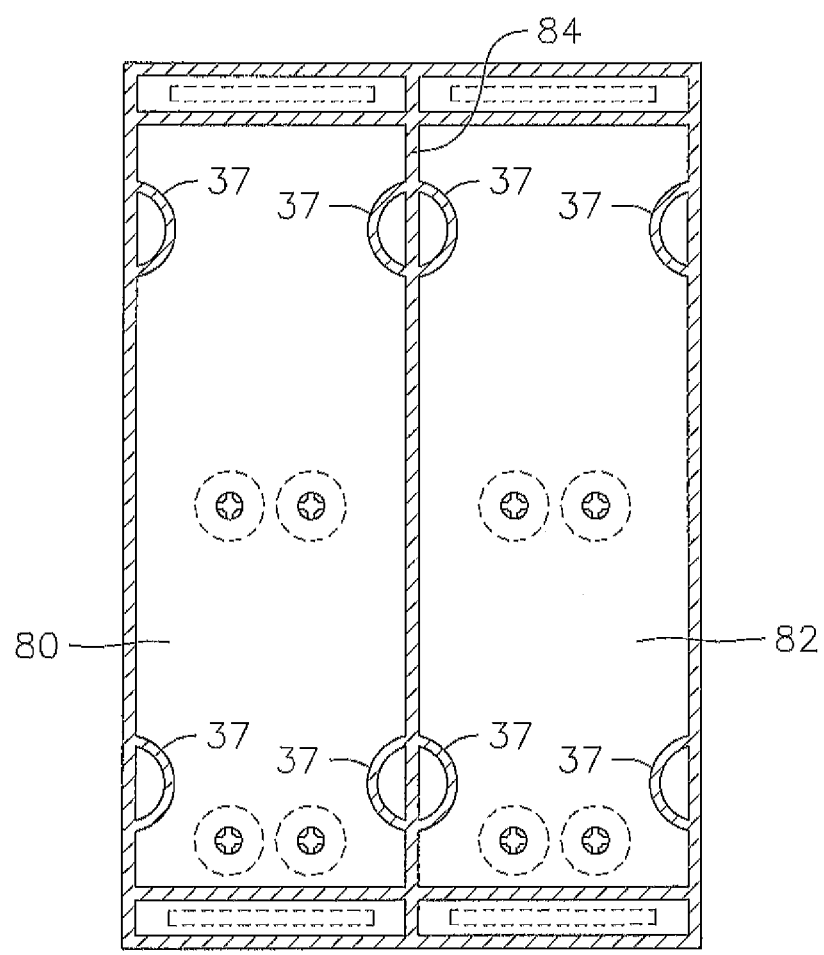

In another exemplary embodiment as for example shown in FIG. 10, applicants have developed dual bag containers 80, 82 which are connected together along one weld line 84. In other words, both biocontainer bags 80, 82 share a common weld line 84. With this invention, two different solutions may be oscillated using a single platform. As can be seen, the inventive multiple compartment bags also designed to be used in the existing platform, as for example by incorporating the rigid support rods 32 at each end which are sealed into segregated areas 33 defined between weld lines. In yet a further exemplary embodiment, any of the relief areas as described in relation with the exemplary embodiment as shown in FIG. 3 may be incorporated in a multiple compartment biocontainer, as for example shown in FIG. 11. Although the bag is being shown with two compartments, the bag may be formed with more than two compartments where adjacent compartments sharing a common weld line. In yet another exemplary embodiment, the relief sections between each compartment can have different geometrical shapes depending on the type of mixing or processing that is required.

Figure 13:
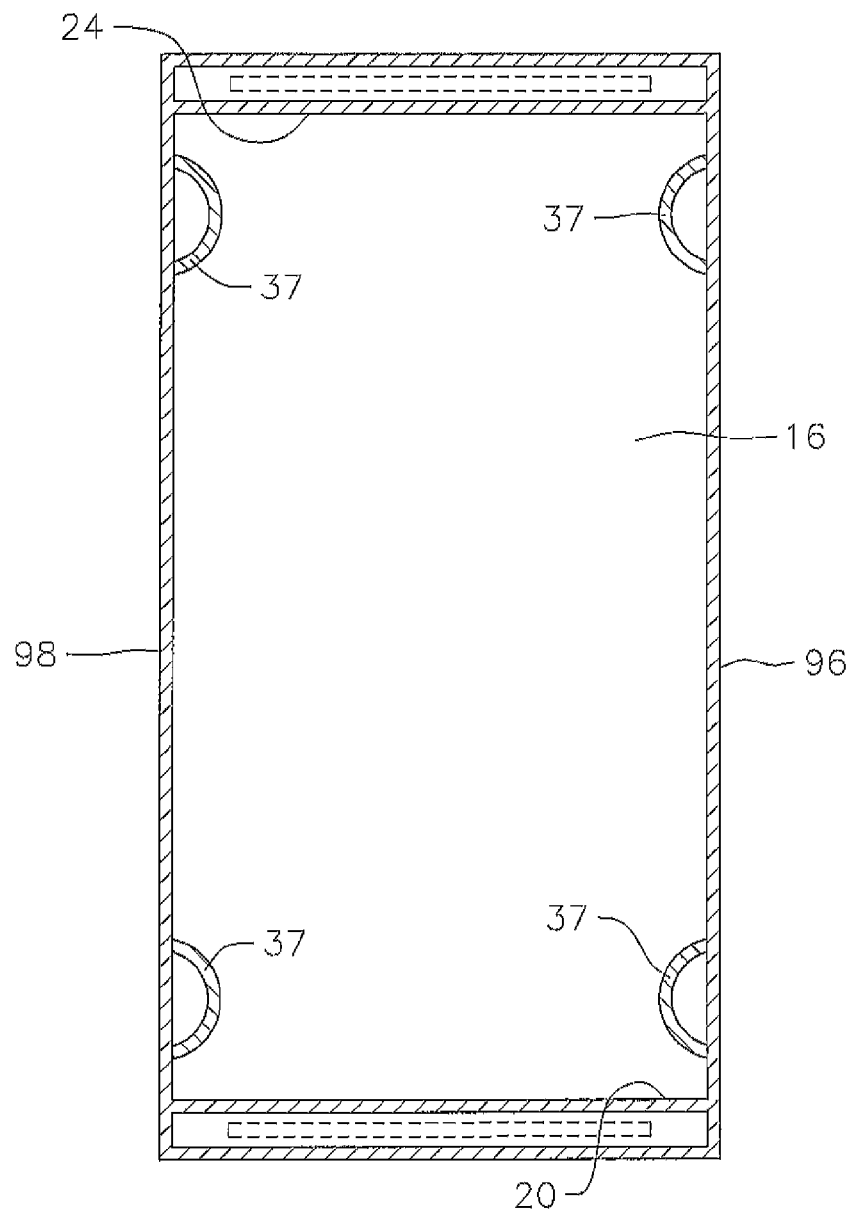
FIG. 13 is a top view of another exemplary embodiment biocontainer of the present invention.
Figure 14:
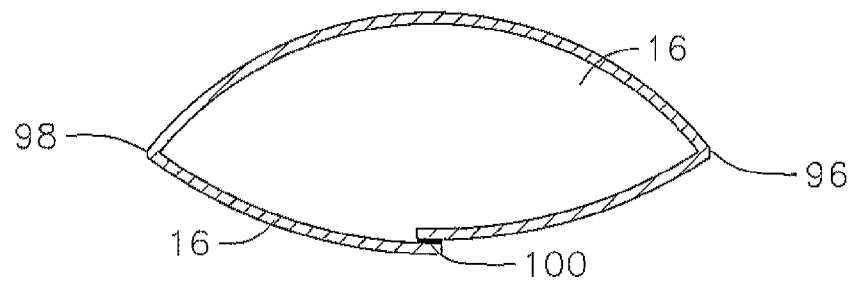
FIG. 14 is a cross-sectional view of another biocontainer.

Although the present invention has been described and illustrated with respect to exemplary embodiments, it is to be understood that it is not so limited, since changes and modifications may be needed which are within the full scope of the invention. For example, the biocontainer bags may have only two seams, as for example 20 and 24 (or only seams 18 and 22 in another exemplary embodiment) plus the seams defining the relief sections 37 as for example shown in FIG. 13. With this embodiment there are no seams along the ends 96 and 98 of the biocontainer bag. In one embodiment the bag may be formed to have a seam 100 along one of the upper portion or lower portion of the film 16, as shown in FIG. 14 where the seam is formed on the lower portion. With this exemplary embodiment, one end of the film 16 is welded or otherwise attached to another end of the film 16 to form seam 100. As can be seen with these embodiments, the biocontainers may be formed from a single film which is folded on to itself to form the upper and lower films (or walls, or layers) of the biocontainer.

What is claimed is:

1. A biocontainer for receiving a fluid comprising:
an outer first flexible wall;
an outer second flexible wall opposite the first flexible wall;
a first end;
a second end opposite the first end;
a third end extending from the first end to the second end;
a fourth end extending from the first end to the second end and opposite the third end;
a first relief section beginning at said first end between the third and fourth ends and extending from said first end toward the second end and being spaced apart from each of said second end, third end and fourth end, wherein the first flexible wall is connected to the second flexible wall along said first relief section, wherein the first flexible wall and the second flexible wall meet at each of said first end, second end, third end, and fourth end, wherein said first end, second end, third end, and fourth end are boundaries of an interior of said biocontainer, wherein said first end defines an interior of said biocontainer and extends from opposite sides of the first relief section for receiving said fluid, and wherein the third end extends from the first end past the first relief section to the second end and wherein the fourth end extends from the first end past the first relief section to the second end; and
a second relief section beginning at said first end between the third and fourth ends and extending from said first end toward the second end and being spaced apart from each of said second, third and fourth ends, wherein the first flexible wall is connected to the second flexible wall along said second relief section and is spaced apart from the first relief section, wherein the first relief section is proximate the third end and the second relief section is proximate the fourth end, wherein said first end extends from opposite sides of said second relief section, wherein the third end extends from the first end past the second relief section to the second end and wherein the fourth end extends from the first end past the second relief section to the second end, wherein when the biocontainer is filled with a fluid it has a depth as measured between the first and second walls, wherein the depth increases from each of said third and fourth ends in a direction along each of said first and second ends transitioning between minimum or no depth at each of the third and fourth ends to an expanded depth at a first distance from said third end and a second distance from said fourth end, wherein said first relief section is located within said first distance and said second relief section is located within said second distance.

2. The biocontainer of claim 1, wherein the first flexible wall is separate from the second flexible wall and is connected to the second flexible wall.

3. The biocontainer of claim 2, wherein the first flexible wall is connected to the second flexible wall along at least one of said ends.

4. The biocontainer of claim 1, wherein the first relief section comprises a separate member connected to the first flexible wall and to the second flexible wall.

5. The biocontainer of claim 1, wherein the first relief section is formed by connecting said first flexible wall directly to said second flexible wall.

6. The biocontainer of claim 1, wherein the first relief section begins and ends at the first end.

7. The biocontainer of claim 6, further comprising:
a third relief section, along which the first wall is connected to the second wall, proximate the third end beginning from and ending at the second end, said third relief section being spaced apart from each of the first end, third end and fourth end and from each of the first and second relief sections; and
a fourth relief section, along which the first wall is connected to the second wall, proximate the fourth end beginning from and ending at the second end, said fourth relief section being spaced apart from each of the first end, third end and fourth end and from each of the first, second, and third relief sections.

8. The biocontainer of claim 7, wherein each of the relief sections is semi-circular in plan view.

9. The biocontainer of claim 7, wherein said third relief section is located within said first distance and said fourth relief section is located within said second distance.

10. The biocontainer of claim 9, wherein the expanded depth is a maximum depth.

11. The biocontainer of claim 7, wherein each of said first, second, third and fourth relief sections are curved or define a geometric shape in plan view.

12. The biocontainer of claim 7, wherein each of said first, second, third and fourth relief sections intersects its corresponding first or second end at an external angle greater than 90°.

13. The biocontainer of claim 1, wherein the expanded depth is a maximum depth.

14. The biocontainer of claim 1, further comprising a seam extending from the third to the fourth ends and being spaced apart from the first and second ends.

15. The biocontainer of claim 1, wherein the first relief section aids in the mixing of a fluid within said biocontainer.

16. The biocontainer of claim 1, wherein a single piece of flexible material is bent over itself and connected along a seam to form the first flexible wall and the second flexible wall.

17. The biocontainer of claim 1, wherein the first flexible wall is separate from the second flexible wall and wherein the biocontainer further comprises:
a first seam along the first end along which the first wall is connected to the second wall;
a second seam along the second end along which the first wall is connected to the second wall opposite the first seam;
a third seam along the third end along which the first wall is connected to the second wall and extending between the first and second seams;
a fourth seam along the fourth end along which the first wall is connected to the second wall and extending between the first and second seams and being opposite the third seam; and
wherein each of the first and second relief sections are also seams connecting the first wall to the second wall.

18. The biocontainer of claim 1, further comprising a rod proximate said third end at a first area and extending externally of said interior in a direction from one of said first end and second end toward the other of said first end and second end.

19. The biocontainer of claim 1, clamped to an oscillating platform proximate said third and fourth ends.

20. The biocontainer of claim 18, further comprising another rod proximate said fourth end at a second area and extending externally of said interior in a direction from one of said first end and second end toward the other of said first end and second end, wherein said another rod is opposite said rod.

21. A biocontainer for receiving a fluid comprising:
a first flexible wall;
a second flexible wall opposite the first flexible wall;
a first end;
a second end opposite the first end;
a third end extending between the first and second ends;
a fourth end extending between the first and second ends and opposite the third end;
a first relief section beginning at said first end between the third and fourth end and extending from said first end toward the second end and being spaced apart from each of said second end, third end and fourth end, wherein said first relief section connects the first flexible wall to the second flexible wall, wherein the first flexible wall and the second flexible wall meet at each of said first end, second end, third end, and fourth end, wherein said first end, second end, third end, and fourth end are boundaries of an interior of said biocontainer, and wherein said first end defines an interior of said biocontainer on opposite sides of the first relief section for receiving said fluid;
a second relief section beginning at said first end between the third and fourth ends and extending from said first end toward the second end and being spaced apart from each of said second, third and fourth ends, wherein said second relief section is spaced apart from the first relief section and connects the first flexible wall to the second flexible wall; and
a rod proximate the third end and extending externally of said interior in a direction from one of said first end and second end toward the other of said first end and second end.

22. The biocontainer of claim 21, further comprising another rod proximate said fourth end and extending externally of said interior in a direction from one of said first end and second end toward the other of said first end and second end, wherein said another rod is opposite said rod.

23. The biocontainer of claim 21, clamped to an oscillating platform proximate said third and fourth ends.

* * * * *